United States Patent
Koppe

(10) Patent No.: US 12,029,672 B2
(45) Date of Patent: Jul. 9, 2024

(54) TECHNICAL ORTHOPAEDIC DEVICE FOR SUPPORTING AN EXTREMITY OF A PATIENT

(71) Applicant: Ottobock SE & Co. KGaA, Duderstadt (DE)

(72) Inventor: Mario Koppe, Göttingen (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 1022 days.

(21) Appl. No.: 15/733,245

(22) PCT Filed: Dec. 11, 2018

(86) PCT No.: PCT/EP2018/084359
§ 371 (c)(1),
(2) Date: Jun. 16, 2020

(87) PCT Pub. No.: WO2019/121165
PCT Pub. Date: Jun. 27, 2019

(65) Prior Publication Data
US 2020/0330253 A1 Oct. 22, 2020

(30) Foreign Application Priority Data

Dec. 20, 2017 (DE) ............. 10 2017 130 685.4

(51) Int. Cl.
*A61F 5/01* (2006.01)
*A61F 5/37* (2006.01)
(Continued)

(52) U.S. Cl.
CPC ............. *A61F 5/013* (2013.01); *A61F 5/3738* (2013.01); *A61H 1/0274* (2013.01);
(Continued)

(58) Field of Classification Search
CPC .... A61F 5/0102; A61F 5/0127; A61F 5/0193; A61F 5/0585; A61F 5/0116; A61F 5/373;
(Continued)

(56) References Cited

U.S. PATENT DOCUMENTS 7,018,351 B1 * 3/2006 Iglesias ................ A61F 5/0111
602/5
9,014,824 B2 4/2015 Kroll-Orywahl et al.
(Continued)

FOREIGN PATENT DOCUMENTS

CN 2808093 Y 8/2006
CN 202892166 U 4/2013
(Continued)

OTHER PUBLICATIONS

Chinese Patent Office; Office Action; CN Appl. No. 201880081772.9; 6 pages.
(Continued)

*Primary Examiner* — Ophelia A Hawthorne
(74) *Attorney, Agent, or Firm* — HOLLAND & HART LLP

(57) ABSTRACT

A technical orthopedic device for supporting an extremity of a wearer. The technical orthopedic device includes at least one support element, on which the extremity rests when the technical orthopedic device is applied. The support element features a support structure and a contact element. The contact element includes or is made of a flat, flexible, preferably elastic material. The contact element is fixed to the support structure in such a way that a gap is created between the contact element and the support structure.

19 Claims, 7 Drawing Sheets

(51) Int. Cl.
*A61H 1/02* (2006.01)
*A61N 1/36* (2006.01)

(52) U.S. Cl.
CPC .............. *A61F 2005/0172* (2013.01); *A61H 2201/1671* (2013.01); *A61H 2201/1697* (2013.01); *A61H 2205/06* (2013.01); *A61N 1/36003* (2013.01)

(58) Field of Classification Search
CPC .... A61F 5/013; A61F 5/05866; A61F 5/0118; A61F 5/3746; A61F 5/37; A61F 5/3738; A61F 5/3723; A61G 13/123; A41D 19/01588; A41D 19/01582
See application file for complete search history.

(56) References Cited

U.S. PATENT DOCUMENTS

| | | |
|---|---|---|
| 2012/0101421 A1 | 4/2012 | Albrecht |
| 2019/0070058 A1 | 3/2019 | Kurzweg et al. |
| 2019/0083289 A1 | 3/2019 | Kurzweg et al. |

FOREIGN PATENT DOCUMENTS

| | | |
|---|---|---|
| CN | 103945799 A | 7/2014 |
| CN | 107106318 A | 8/2017 |
| DE | 10 2010 049 191 A1 | 4/2012 |
| DE | 10 2011 018 470 A1 | 10/2012 |
| DE | 10 2016 104 880 A1 | 9/2017 |
| EP | 0346697 A2 | 12/1989 |
| EP | 1006960 A1 | 6/2000 |
| EP | 2076224 B1 | 9/2007 |
| JP | 2014-113666 A | 6/2014 |
| WO | 2009029693 A1 | 3/2009 |

OTHER PUBLICATIONS

International Search Report for International Application No. PCT/EP2018/084359, mailed 22 Mar. 22, 2019, 12 pages.

* cited by examiner

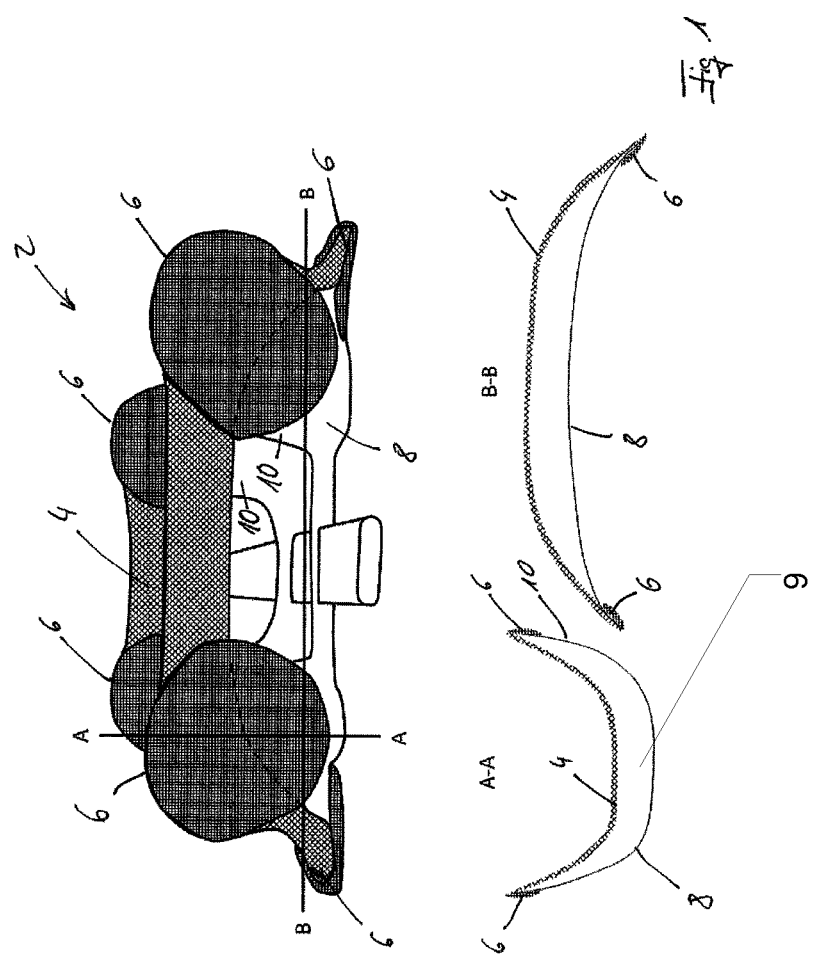

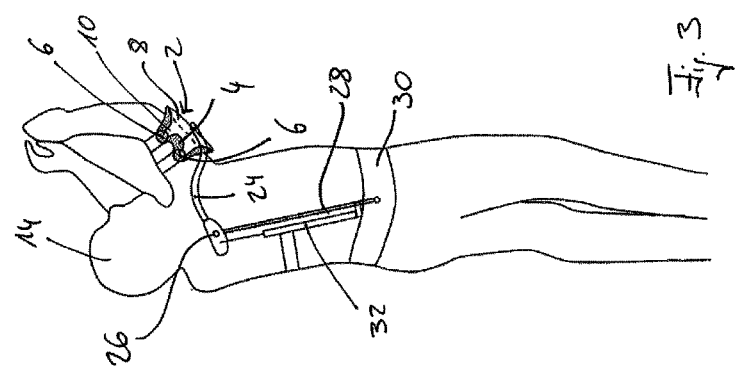
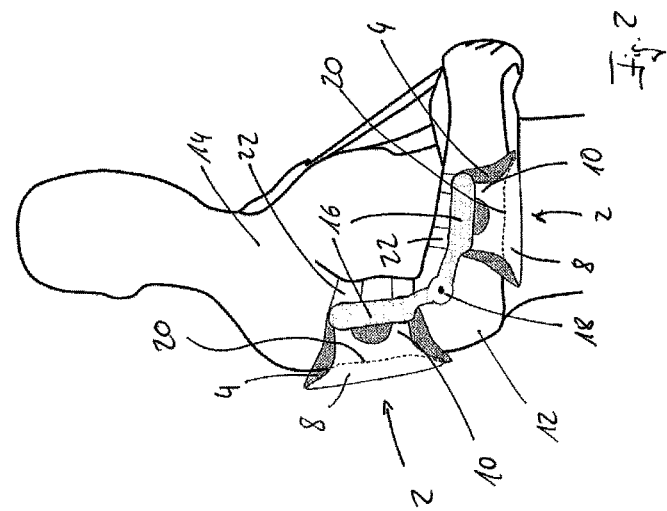

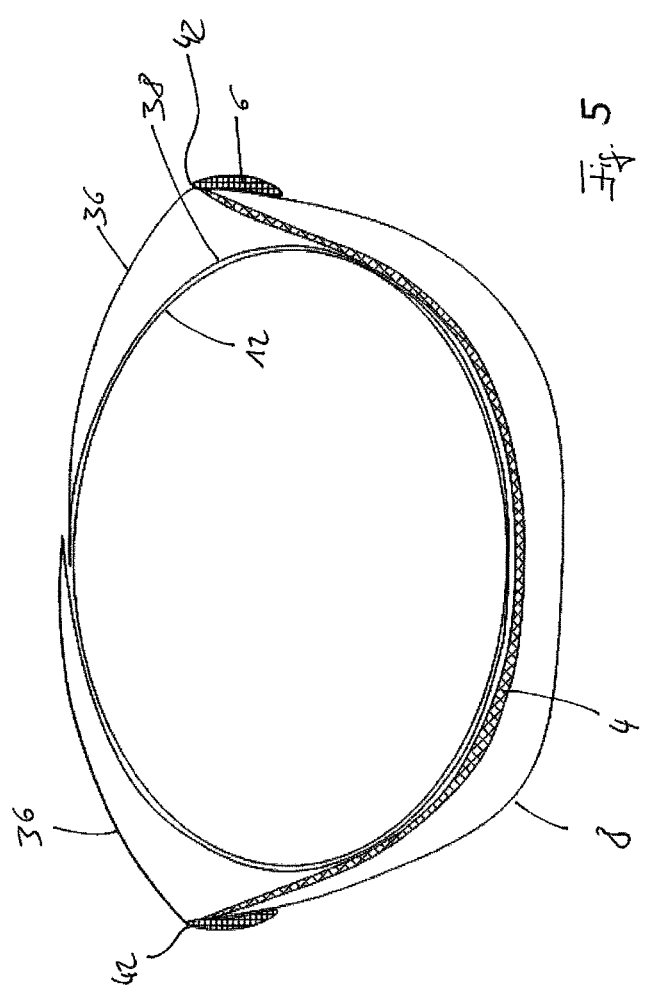

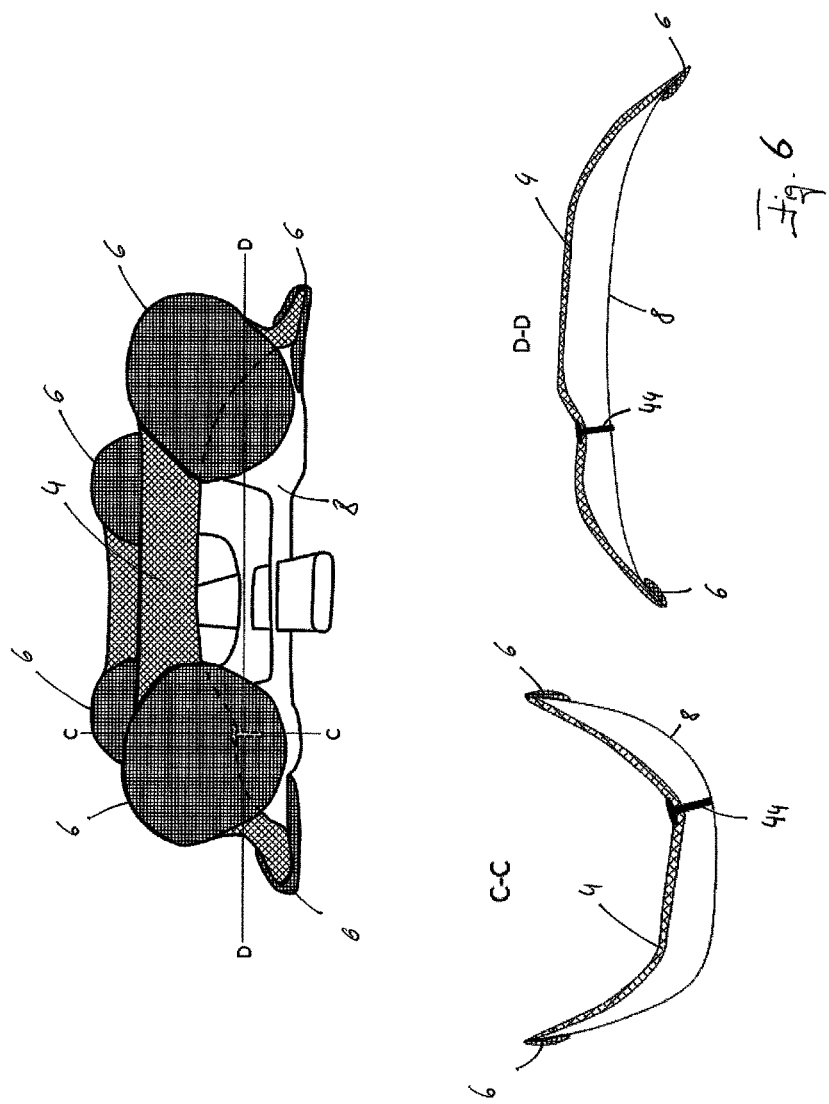

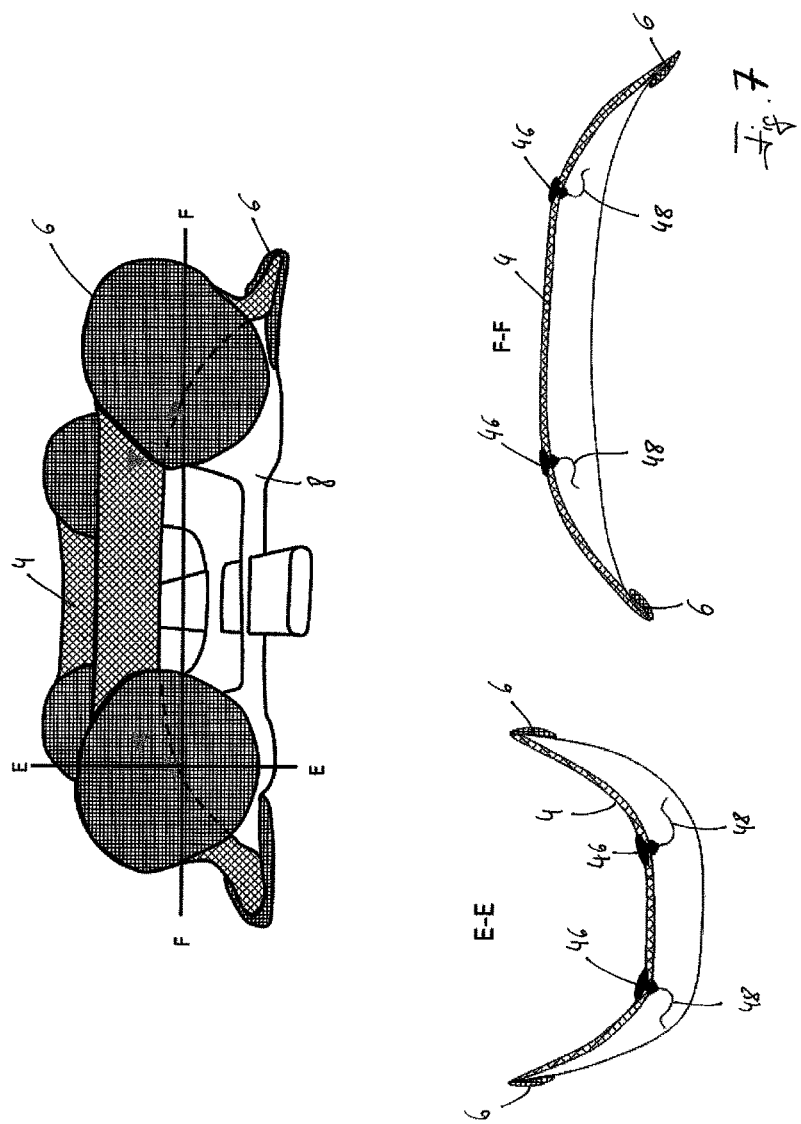

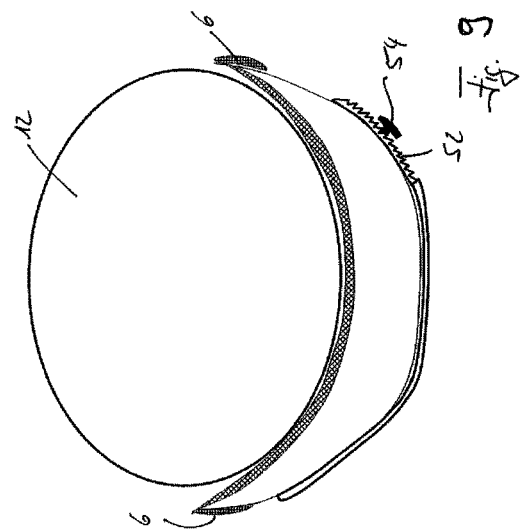
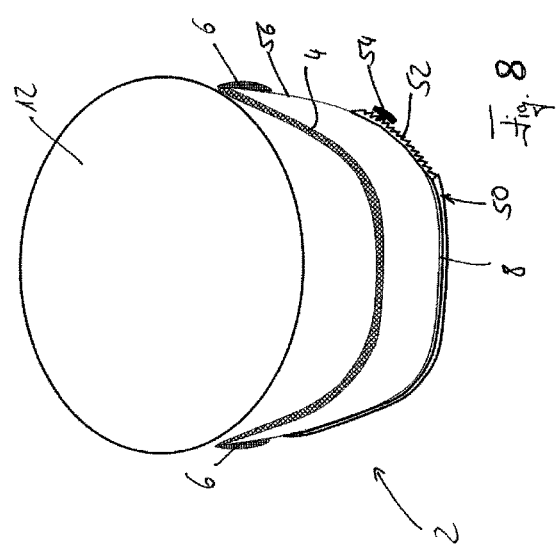

TECHNICAL ORTHOPAEDIC DEVICE FOR SUPPORTING AN EXTREMITY OF A PATIENT

CROSS REFERENCE TO RELATED APPLICATIONS

This application is a U.S. National Entry and claims priority to PCT International Patent Application No. PCT/EP2018/084359, filed 11 Dec. 2018, and entitled "TECHNICAL ORTHOPAEDIC DEVICE FOR SUPPORTING AN EXTREMITY OF A PATIENT", which claims priority to Germany Patent Application No. 10 2017 130 685.4 filed 20 Dec. 2017, the entire disclosures of which are incorporated herein by this reference.

TECHNICAL FIELD

The invention relates to a device for supporting an extremity of a wearer, wherein the device comprises at least one support element, on which the extremity rests when the device is applied, wherein the support element has a support structure and a contact element, wherein the contact element comprises or is made of a flat, flexible, preferably elastic material.

BACKGROUND

Such devices have been known within the scope of the prior art for many years, for example in the form of orthoses. In the scope of the present invention, the term device should also be understood to mean exoskeletons of a certain shape or other supporting devices. For example, DE 2016 104 880 A1, which has not been pre-published, describes a supporting device which serves to facilitate work performed above a user's head by applying a force against gravity to the upper arm of the wearer. Other orthoses, such as arm abduction orthoses or shoulder orthoses, are intended to immobilize a joint, such as an elbow or a shoulder, and prevent a movement. In the case of arm abduction orthoses in particular, the arm must be held in a raised position, for which it is laid on a support element.

Such support elements often consist of a shell made of a rigid component or other flat objects that are equipped with padding, such as a cushion or a foam, if necessary. Nevertheless, pressure sores, an unpleasant build-up of sweat or even an interruption to blood circulation often occur, especially with devices worn over a long period of time, the latter resulting from a possible pressure on the blood vessels. In particular, shell elements made from a rigid material, such as carbon fiber composite material, plastic or metal, are generally not adapted to the individual circumstances of the respective wearer, but rather are a standard shape. However, this is not the optimal shape, meaning that the specified disadvantages often arise.

SUMMARY

The invention therefore aims to further develop the type of device initially referred to in such a way that the disadvantages named are avoided or at least considerably mitigated.

The invention solves the problem by way of a device according to the features disclosed herein, wherein the contact element is fixed to the support structure in such a way that a gap is created between the contact element and the support structure. This gap is designed such that it is also present when the device is applied.

The extremity of the wearer, such as a leg or an arm, is laid on the contact surface of the support element in such a way that the material characteristics optimally adapt to the shape of the respective body part. As a result, little consideration has to be given to the individual circumstances, other than the fact that different sizes of the device may have to be provided. It is ensured that the flat and flexible material optimally adapts to the extremity. Specifically, this can be achieved by ensuring that it is not arranged over the entire surface of the actual support structure, but in such a way that the gap emerges, into which the material of the contact element can drop and the contact element can deform, when a body part exerts a load on it. Here, the dimensions of the gap are such that it may become smaller as a result of the deformation of the contact element but, due to the forces that occur upon proper use, it does not close. These forces are exerted by the extremity supported by the support element.

The contact surface is preferably connected to the support structure at several fixing points spaced apart from one another. Here, it is advantageous if the fixing points are arranged on two opposite sides of the extremity. For example, if an upper arm is to be supported by the device, it is advantageous to arrange the fixing points on two opposite sides of the arm, for instance on the medial and lateral side, so that the flat, flexible material of the contact element extends between them. As a result, the extremity of the wearer that is laid on the contact element preferably does not come into contact with the fixing points; in particular, it does not come into contact with the actual support structure between the fixing points. This ensures the prevention of both pressure sores and interruptions to blood circulation. In addition, the flat, flexible material, which is preferably designed to be elastic, is much lighter than a shell made from metal or a plastic, for example.

Preferably, the contact element is fixed to the support structure at at least three, preferably at least four, especially preferably at least six fixing points, or at a circumferential fixing point, preferably on a circumferential edge of the support structure. In this case, at least two fixing points are arranged on at least one, but preferably on both sides of the extremity, i.e. medially and laterally for example. This ensures an optimal mounting of the extremity on the contact element.

Alternatively, the contact element can also be connected to the support structure at a single fixing point if said fixing point extends across a section of the circumference, preferably across the entire circumference, of the contact element.

In a preferred configuration, the contact element is at least partially, but preferably completely, made of a material that is permeable to air. This prevents an unpleasant build up of sweat and ensures sufficient air circulation. To this end, it is particularly advantageous if a distance between the contact element and the support structure is selected in such a way that air circulation can also occur at this point. Of course, this does not apply to the fixing points, as here, the contact element is fixed to the support structure.

Preferably, the contact element is at least partially, but preferably completely, made of a foil, a mesh, a textile such as an air-permeable fabric, a perforated padding material such as a foam or an elastomer, or an auxetic material. An auxetic material in particular need not be designed to be elastic; rather, it can just be flexible. For instance, it may be made from TPE. In the case of a foil, it has been proven beneficial for it to be perforated, i.e. equipped, in particular, with a hole pattern, to ensure air circulation, for example, and to turn the foil into an air-permeable material. This is not necessary with a mesh or a textile, as these structures already feature enough perforations which allow air to circulate.

Preferably, the support structure is or comprises a plastic component, a metal component or a component made of a fiber composite. The fixing points preferably protrude from the rest of the support structure in the form of tabs. The contact element can preferably be fixed to the support structure such that it can be detached. For example, this may occur via velcro fasteners, press stud elements, other positive-locking elements or adhesive bonds. Due to the detachable connection, the actual contact element can be removed from the support structure when the device is not in use and washed, for instance, so as to allow the device to be reused. Of course, a contact element may also be replaced with another contact element in this way, the other contact element being made of another material, exhibiting a different degree of stiffness or having other physical and/or chemical properties. For example, it is thus possible to provide a fabric whose fibers are at least partially made of silver or coated with silver to achieve an anti-bacterial effect.

The distance between different fixing points is preferably adjustable, for which a cable system or traction system is preferably used. By adjusting the distance between the individual fixing points, the tension of the flat and flexible, preferably elastic material of the contact element changes, wherein said contact element extends between the fixing points. The tension and the distribution of tension can thus be individually adapted to achieve optimal distribution.

Preferably, the device features at least one actuator, which is preferably driven, wherein a distance between the at least two fixing points can be altered by the actuator. In this case, the at least one actuator can be driven hydraulically, pneumatically or in another way, for instance. As a result, it is possible, for example, to set a time sequence of different tensions and distributions of tension in the flat, flexible material of the contact element and thus, for instance, support the extremity resting on the contact element and change the distribution of pressure. This is especially advantageous for devices that are worn over a very long period of time and that support the extremity of the wearer. This prevents, for example, pressure sores from forming. The adjustability can also be achieved by way of at least one tension element, wherein the tensile force transferred by the tension element can be adjusted, for instance, with a rotatable activation element. This type of tension element is described in EP 2 076 224 B1, for instance.

In a preferred configuration, the device has at least a second support element, which is arranged on a side of the extremity that faces away from the first support element when the device is applied. Such a second support element may be designed to be identical or different to the first support element and to accommodate every configuration that has been described for the first support element. The arrangement on two opposite sides of the extremity allows for a comprehensive support. In this way, in the case of a drooping arm, for example, a first support element is arranged on the back side (ventrally), the fixing points of which are found to the right and left (medially and laterally) of the upper arm. A second support element is arranged frontally in relation to the upper arm, wherein the fixing points are also situated medially and laterally, i.e. to the right and left, of the upper arm. As a result, an almost complete support of the extremity, in this case the upper arm, is possible. This is especially advantageous if the extremity is to be rested in different positions relative to the direction of gravity, as the wearer can also assume different positions.

The device is preferably a technical orthopedic device, such as an orthosis, a mounting device, a rehabilitation device or part of an exoskeleton.

Preferably, a sensor and/or at least one electrode is arranged on the contact element. The at least one sensor and/or the at least one electrode comes into contact with the extremity and especially the skin of the wearer when the device is applied. As a result, the electrode can capture electrical signals, such as myoelectric signals, which can be transmitted to an electric control system or an evaluation unit. Alternatively or additionally, electrical signals can also be transmitted to the skin of the wearer to stimulate muscles found beneath the skin, for instance. If a sensor is used, the pressure, for example, can be determined; it can then be identified whether sufficient padding has been provided. Alternatively or additionally, a moisture level of the skin, a spatial position, an absolute angle or another variable can also be determined, which can then be used to monitor the device and/or control functions of the device.

To avoid a pressure sore, the contact element can be relieved of tension at a desired point to create relief at a specific point. This is practical if, for instance, the extremity of the wearer of the device has osseous projections or sensitive spots, such as a wound, an ulceration or other areas that need to be relieved of pressure. Pins, pulleys or flexible and/or elastic units can be used to achieve a relief of pressure.

BRIEF DESCRIPTION OF THE DRAWINGS

In the following, examples of embodiments of the present invention will be explained in more detail by way of the attached figures: They show FIG. 1—the schematic depiction of a part of a device according to a first example of an embodiment of the present invention with two sectional representations, FIG. 2—a device in the form of an arm orthosis, FIG. 3—the schematic depiction of an applied device according to another example of an embodiment of the present invention, FIGS. 4 and 5—the schematic representations of another embodiment in the opened and closed state, FIGS. 6 and 7—schematic side and sectional representations of a part of a device according to a further example of an embodiment of the present invention, FIGS. 8 and 9—schematic representations of a device according to another example of an embodiment of the present invention.

DETAILED DESCRIPTION

Figure 4:
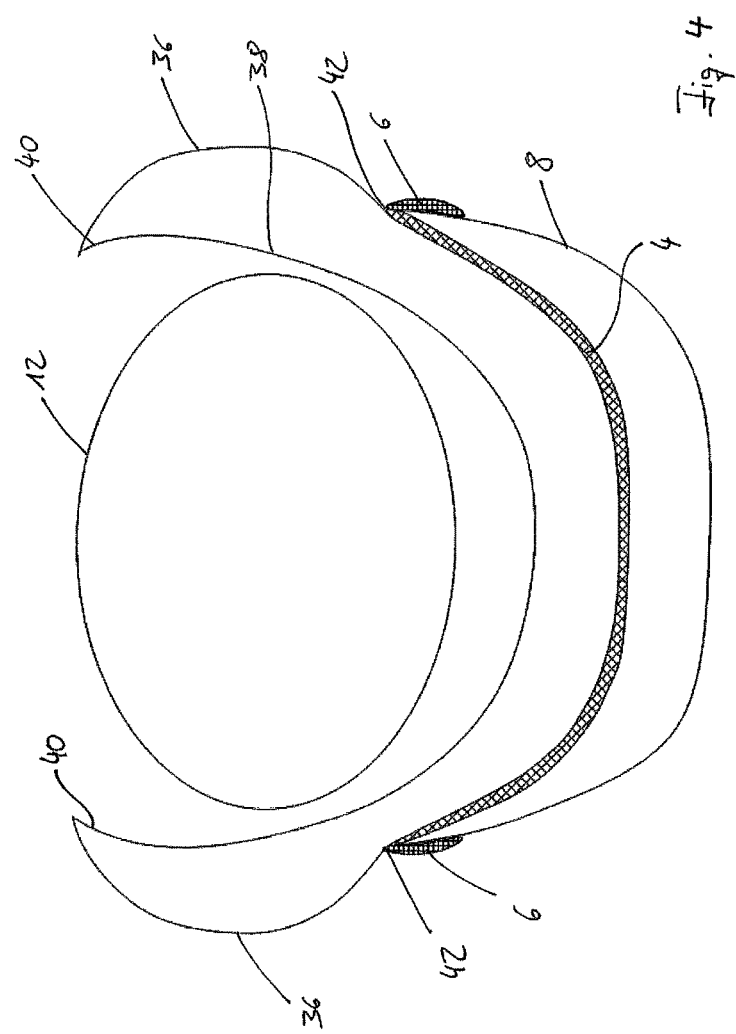

The upper part of FIG. 1 contains a schematic 3D view of a support element 2 for a device according to a first example of an embodiment of the present invention. The support element features a contact element 4 that is fixed to a support structure 8 at six fixing points 6 to define a gap 9. The individual fixing points 6 are arranged as separate components on the rest of the support structure 8. The lower part of FIG. 1 depicts the two sectional representations along the lines A-A and B-B.

The left-hand lower part of FIG. 1 depicts the sectional representation along the line A-A. The support structure 8, which is curved in this section, can be recognized; the fixing points 6 are situated at the upper ends of said support structure. The contact element 4 is arranged at these ends. The right-hand lower part of FIG. 1 depicts the sectional representation along the line B-B. The support structure 8 can also be recognized here; however, in this section representation, it is curved the other way. There are also two fixing points 6 at the end, on which the contact element 4 is arranged. If an extremity, such as an arm of a wearer, is now inserted into the support element 2 according to FIG. 1, the contact element 4 can optimally adapt to the geometric shapes and contours of the extremity. The fixing points 6 are preferably arranged on projections 10 of the support structure 8, such that an elasticity is achieved to at least a small extent; however, such an elasticity is preferably already achieved as a result of the material of the support structure 8 itself.

FIG. 2 features a representation of a device that is arranged on an arm 12 of a wearer 14. The device has two support elements 2, one of which is arranged on the upper arm and the other on the lower arm of the wearer 14. The two are connected to one another via splints 16 and a joint 18 between said splints.

The two contact elements 4 can be seen, which are again designed as mesh structures and rest on the arm 12 of the wearer 14. The support structure 8 features projections 10, on which the fixing points 6 are situated.

The outer contours of the upper arm and lower arm of the wearer 14 are depicted with a dashed line 20. It is clear that they are situated at a distance to the support structure 8, so that the arm 12 of the wearer 14 does not come into contact with any potentially rigid or stiff components of the support elements 2. The only contact on this side of the respective arm 12 is preferably with the contact element 4. The device is held on the wearer 14 via straps 22.

FIG. 3 shows another embodiment of a device, which has a support element 2 that again features the support structure 8 with the projections 10 and the fixing points 6, on which the actual contact element 4, again in the form of a mesh-like structure, is arranged. The device according to FIG. 3 comprises a lever element 24 that is connected via a joint 26 to a force transmission device 28, which transmits a force to be applied to a belt element 30 and thus to the wearer 14. A force application element 32 is situated between the lever element 24 and the force transmission element 28, wherein said force application element can be used to apply a force to the lever element 24 and therefore to the support element 2.

FIG. 4 depicts the support structure 8 with the attached contact element 4 in another configuration according to the present invention. The contact element 4 is arranged on the support structure 8 via the fixing points 6. The device also has two shell elements 36, between which an activation element 38 is arranged. An arm 12 of the wearer is also schematically depicted. This arm 12 can be inserted from above through the opening between the two shell elements 36. To this end, it is being moved downwards in FIG. 4, thereby coming into contact with the activation element 38, whose end zones 40 are attached to the shell element 36. If the arm 12 from the situation depicted in FIG. 4 is moved further downwards, a downward force is exerted on the activation element 38, this force ensuring that the two shell elements 36 swivel around about joints 42.

This results in the situation shown in FIG. 5. The arm 12 is almost completely surrounded by the activation element 38. As a result of its downward movement, it has swivelled the two shell elements 36 about the joints 42, thereby closing the arrangement.

FIGS. 6 and 7 depict the views of a device from FIG. 1 according to another example of an embodiment of the present invention, which is different to the configuration shown in FIG. 1. The contact element 4 is fixed to the support structure 8 at six fixing points 6. In the lower two sectional representations of FIG. 6 in particular, a brace element 44 can be seen, which connects the contact element 4 and the support structure 8 at another point. This changes the shape of the contact element 4 at this point and results in a relief of strain at the specific point.

FIG. 7 shows the same views of part of another configuration of the present invention. In the example of an embodiment shown, electrodes 46 are inserted into the contact element 4, wherein said electrodes come into contact with the skin of the wearer when the device is applied and can thus direct, for instance, electrical signals away from the skin or to the skin. Alternatively or additionally, sensors can be used that should come into contact with the skin. The electrical signals are directed to the electrode 46 or away from the electrode 46 via schematically depicted electrical lines 48.

FIGS. 8 and 9 show a configuration of the present invention, the width of which is adjustable. FIG. 8 features an arm 12 that is to be inserted into a support element 2 according to an example of an embodiment of the present invention. As in the previous examples of an embodiment shown, the contact element 4 is arranged on the support structure 8 via fixing points 6. In the example of an embodiment shown, the length of this support structure 8 is adjustable. A first component 50 comprises a row of teeth 52 with which a ratchet element 54 of a second component 56 can engage. While in FIG. 8 the distance between the two illustrated fixing points 6 is too small to accommodate the arm 12, this has been changed in FIG. 9. The arm 12 fits between the two fixing points 6, as the ratchet element 54 engages in another tooth of the row of teeth 52.

I claim:

1. A device for supporting an extremity of a wearer, the device comprising:
    at least one support element on which the extremity rests when the device is applied, the at least one support element comprising:
        a support structure; and
        a contact element made of a flat, flexible material, wherein the contact element is fixed to the support structure in such a way that the contact element creates a gap between the contact element and the support structure, wherein the contact element is fixed to the support structure by at least three fixing points or at a circumferential fixing point of the support structure.

2. The device according to claim 1, wherein a distance between the at least three fixing points is adjustable.

3. The device according to claim 2, wherein the device comprises at least one actuator operable to change the distance between the at least three fixing points.

4. The device according to claim 3, wherein the at least one actuator is a driven actuator.

5. The device according to claim 2, wherein the distance between the at least three fixing points is adjustable using a cable system or a traction system.

6. The device according to claim 1, wherein the contact element is made at least partially from a material that is permeable to air.

7. The device according to claim 6, wherein the contact element is made completely from a material that is permeable to air.

8. The device according to claim 1, wherein the contact element is at least partially made of a foil, a mesh, a textile such as an air-permeable fabric, a perforated padding material such as a foam or an elastomer, or an auxetic material.

9. The device according to claim 8, wherein the contact element is completely made of a foil, a mesh, a textile, a perforated padding material, or an auxetic material.

10. The device according to claim 1, wherein the support structure comprises a plastic component, a metal component or a component made of a fiber composite, and the at least three fixing points protrude from the rest of the support structure.

11. The device according to claim 10, wherein the at least three fixing points protrude from the rest of the support structure in the form of tab s.

12. The device according to claim 1, wherein the contact element is detachably fixed to the support structure.

13. The device according to claim 1, wherein the at least one support element includes first and second support elements, the second support element is configured to be arranged on a side of the extremity that faces away from the first support element when the device is configured to be applied to the extremity.

14. The device according to claim 1, wherein the device is a technical orthopaedic device, the technical orthopaedic device including at least one of an orthosis, a mounting device, a rehabilitation device, or an exoskeleton.

15. The device according to claim 1, wherein the at least three fixing points includes at least six fixing points.

16. A device for supporting an extremity of a wearer, comprising:
at least one support element to support the extremity when the device is applied to the extremity, the support element comprising:
a support structure;
a contact element comprising a flat, flexible, elastic material, the contact element being coupled to the support structure, wherein the contact element is coupled to the support structure at least three fixing points, and wherein a distance between the at least three fixing points is adjustable; and
a gap provided between the contact element and the support structure.

17. The device according to claim 16, wherein the contact element is made at least partially from a material that is permeable to air.

18. The device according to claim 16, wherein the contact element is at least partially made of a foil, a mesh, a textile, a perforated padding material, or an auxetic material.

19. A device for supporting an extremity of a wearer, the device comprising:
at least one support element on which the extremity rests when the device is applied, the at least one support element comprising:
a support structure; and
a contact element made of a flat, flexible material, wherein the contact element is fixed to the support structure in such a way that the contact element creates a gap between the contact element and the support structure, wherein the contact element is fixed to the support structure at least three fixing points that protrude from the rest of the support structure in the form of tabs.

* * * * *